United States Patent [19]

Blatchford et al.

[11] 4,215,442
[45] Aug. 5, 1980

[54] MULTI-BAR LINKAGE KNEE WITH FIXED ROTATION AXIS

[75] Inventors: Brian G. Blatchford, Basingstoke; Victor J. Woolnough, Kempshott, Nr. Basingstoke, both of England

[73] Assignee: Chas. A. Blatchford & Sons Limited, Basingstoke, England

[21] Appl. No.: 946,371

[22] Filed: Sep. 27, 1978

[30] Foreign Application Priority Data

Sep. 28, 1977 [GB] United Kingdom ............... 40343/77

[51] Int. Cl.³ ........................... A61F 1/04; A61F 1/08
[52] U.S. Cl. ............................................................. 3/22
[58] Field of Search ........................ 3/22, 29, 26, 28, 2

[56] References Cited

U.S. PATENT DOCUMENTS

| | | | |
|---|---|---|---|
| 3,820,169 | 6/1974 | Long et al. | 3/22 |
| 3,823,424 | 7/1974 | May | 3/22 |
| 4,064,569 | 12/1977 | Campbell | 3/26 |

*Primary Examiner*—Clifford D. Crowder
*Attorney, Agent, or Firm*—Cushman, Darby & Cushman

[57] ABSTRACT

An artificial leg employs a knee mechanism having a multi-bar linkage (1, 3, 4, 7, 9, 12). The leg is intended for patients having a disarticulated knee amputation or an above-knee amputation with a long thigh stump, the mechanism being situated in the upper part of the calf. The geometry of the linkage is such that the mechanism has a fixed or virtually fixed axis of rotation (16) which is projected outside the confines of the mechanism into the space occupied by the end portion of the stump. Since the mechanism is uniaxial and internal, a relatively good external appearance can be obtained.

13 Claims, 3 Drawing Figures

# MULTI-BAR LINKAGE KNEE WITH FIXED ROTATION AXIS

BACKGROUND OF THE INVENTION

This invention relates to an artificial leg having a knee mechanism comprising a multi-bar linkage.

The use of multi-bar linkages, particularly four-bar linkages, in the knee mechanisms of artificial legs is well-known. Six-bar linkages have also been used but are less common.

Normally, a knee mechanism incorporating a multi-bar linkage has an axis of rotation whose position moves according to the degree of flexion of the knee. This feature has been employed by designers to produce a leg in which the axis of rotation is relatively high at full extension and descends towards the natural knee centre with increasing flexion of the knee. A leg having these characteristics is of particular use for a patient with a weak thigh stump, since a high initial instantaneous axis of rotation enables the patient to initiate flexion with relatively little muscular effort. If the initial axis is sufficiently high, the leg can be made to have positive stability at heel contact, i.e. at full extension.

However, a linkage with a moving axis of rotation as described above has the disadvantage that, during the initial stage of flexion from the fully extended position, the lower end of the thigh moves forward appreciably in a near-linear manner relative to the top of the shin. This can cause considerable difficulty in obtaining a neat cosmetic appearance in the region of the knee.

It is relatively easy to provide a reasonable cosmetic appearance with a leg having a uniaxial knee mechanism, i.e. a mechanism with a single, fixed axis of rotation. Therefore, in cases where the patient is relatively strong and can exert sufficient muscular control, the more common uniaxial mechanism with a single rotating bearing may be preferred. However, a patient with a disarticulated knee amputation ("through-knee amputation") cannot use the normal internal uniaxial mechanism since the stump extends into the space needed to accommodate the mechanism. The same applies to a patient with an above-knee amputation having a very long stump; there is insufficient room for even the most compact of known internal uniaxial knee mechanisms. In such cases it is conventional to provide a leg with external side joints. In comparison with a leg having an internal joint, one with side joints is unsightly, and has the further disadvantage that it is difficult to incorporate effective or neat control mechanisms, for example a knee lock or a swing control.

SUMMARY OF THE INVENTION

It is an object of this invention to provide an artificial leg of the multi-bar type which is suitable for a patient having a through-knee amputation or an above-knee amputation with a long stump, and which largely avoids the cosmetic disadvantages mentioned above. This is accomplished by arranging the linkage such that the leg has a fixed or virtually fixed knee axis of rotation, with the knee mechanism situated wholly or mainly below the said axis.

Thus instead of being used to generate a moving axis of rotation which descends from an initial high position to a position in which it passes through the mechanism itself, in an artificial leg in accordance with this invention, the multi-bar linkage produces an axis of rotation which remains virtually stationary outside or just inside the physical outline of the mechanism throughout the range of knee flexion. This results in a leg which can be fitted to patients with very long thigh stumps and yet, due to the mechanism being internal and uniaxial, can be provided with a neat cosmetic covering.

In the preferred embodiment of the invention the knee axis lies outside the physical confines of the mechanism and in approximately the same position as the effective or average knee centre of the natural leg. A leg designed for a patient with a disarticulated knee amputation has an axis of rotation which passes through the space occupied by the end part of the stump.

The mechanism preferably comprises a six-bar linkage in which two of the links are constituted respectively by an upper leg component to be fitted to the patient's stump and a lower leg component attached to the shin. The other four links are formed by pivotally interconnected members which are movable with respect to both leg components, two of these four links having three pivot axes defining pivot connections with other links. The linkage is housed within the upper part of the shin. A spring or a length of elasticated cord connecting two links of the linkage may be included to provide an extension bias. A swing control such as a pneumatic swing phase control and a stance control such as a knee lock may also be incorporated.

Since the mechanism is internal, the leg may be of the endoskeletal type, i.e. it can be provided with a continuous outer covering. In the case of an endoskeletal leg, the preferred mechanism has the advantage that the arrangement of the links is such that, from full extension to full flexion of the knee, no part of the mechanism extends outwardly sufficiently to cause an unsightly protrusion.

It should be noted that a natural knee joint is not strictly uniaxial; there is a small movement of the axis of rotation as the knee is flexed. Similarly the artificial leg of this invention does not necessarily have a strictly fixed axis, and it is intended that the expression "virtually fixed" in the claims and the foregoing description should include a mechanism in which the position of the axis does exhibit relatively small movements. In a mechanism with a six-bar linkage, movements of the axis may be due to play in the large number of pivoting joints. In certain circumstances a very limited amount of designed movement of the axis can be beneficial.

BRIEF DESCRIPTION OF THE DRAWINGS

The invention will now be described by way of example with reference to the drawings in which.

DESCRIPTION OF THE PREFERRED EMBODIMENT

Figure 1:
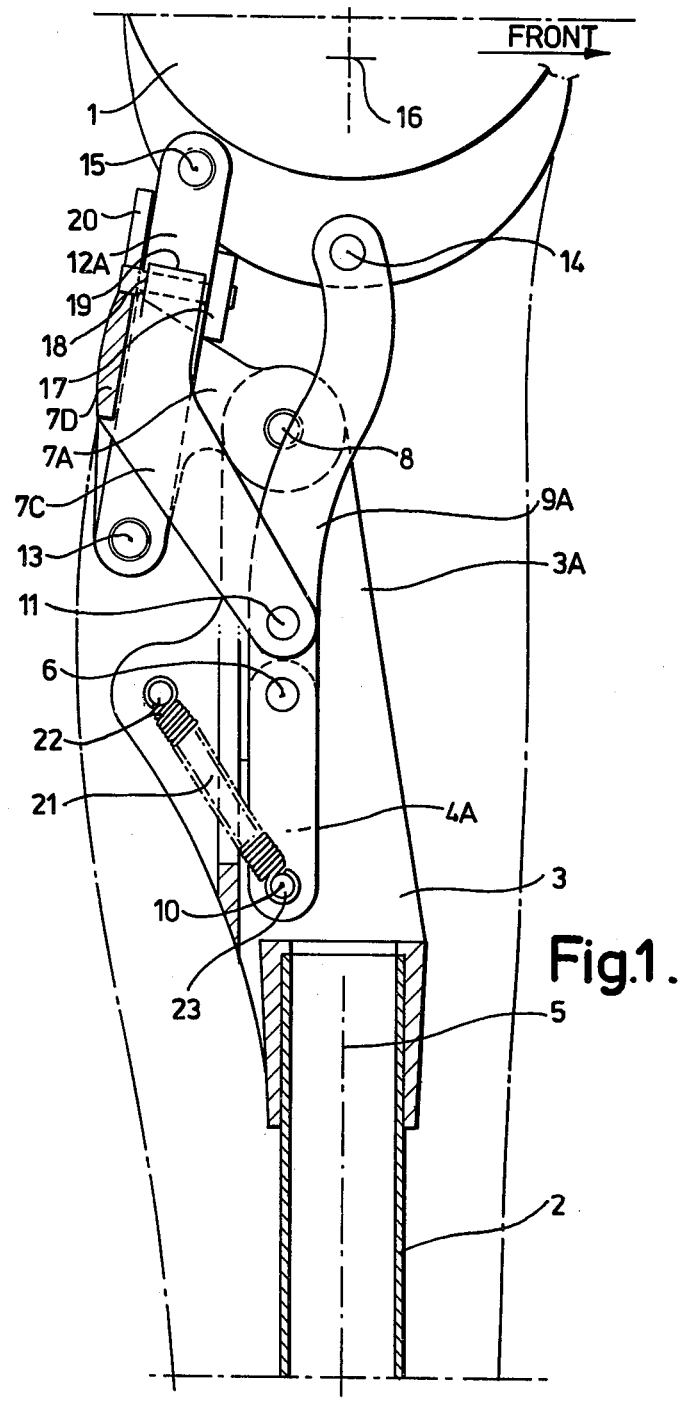
FIG. 1 is a section on the plane I—I of FIG. 2 of part of an artificial leg with a six-bar linkage knee mechanism, with some components shown in elevation.

The mechanism shown in the drawings comprises a six-bar linkage connecting an upper leg component 1 which is fitted to the patient's thigh stump and a lower leg component including a shin tube 2 and shin cradle 3.

Figure 2:
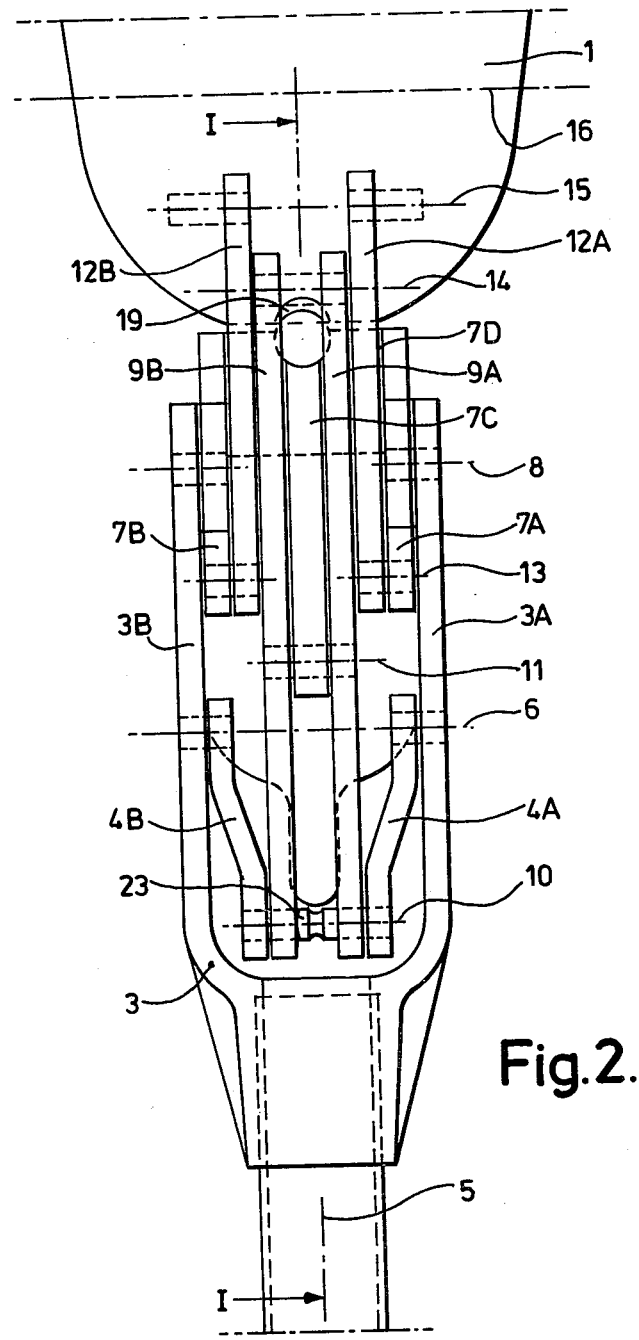
FIG. 2 is a front elevation of the leg of FIG. 1.

The six "bars" or links of the linkage may be listed as follows. (Some of the links are constituted by pairs of members arranged symmetrically on either side of the longitudinal axis of the leg; these paired members are best seen in FIG. 2).

Link I is formed by the shin cradle 3 having two side arms 3A and 3B;

Link II is formed by a pair of two relatively short connecting members 4A and 4B which are arranged symmetrically on either side of the longitudinal axis 5 of the leg. Members 4A and 4B are pivotable with respect to link I about the axis 6;

Link III is formed by the combination of two side members 7A and 7B and the central member 7C. These three members are rigidly connected together by a cross member 7D shown in section in FIG. 1. Link III has three pivot connections to other links, including one to the shin cradle 3 along axis 8;

Link IV is another three-pivot link and is formed by the paired members 9A and 9B. Connections to links II and III are made along pivot axes 10 and 11 respectively;

Link V is formed by the paired members 12A and 12B, and pivots relative to link III about axis 13;

Finally, link VI is the upper leg component 1 which has two pivot connections defined by axes 14 and 15 to links IV and V respectively.

This gives a total of six links connected together at seven pivot axes. The effective dimensions of each link (i.e. the lengths of straight lines drawn between the pivot axes of each link) are chosen in such a way that the shin cradle 3 is rotatable relative to the upper leg component 1 about an axis of rotation 16 which is fixed relative to the shin, and which, as can be seen from FIGS. 1 and 3, passes directly through the upper leg component and the space formed therein for the end portion of the patient's stump. In other words, the axis of rotation 16 is outside the physical confines of the knee mechanism as represented by the pivot connections and members joining them.

Figure 3:
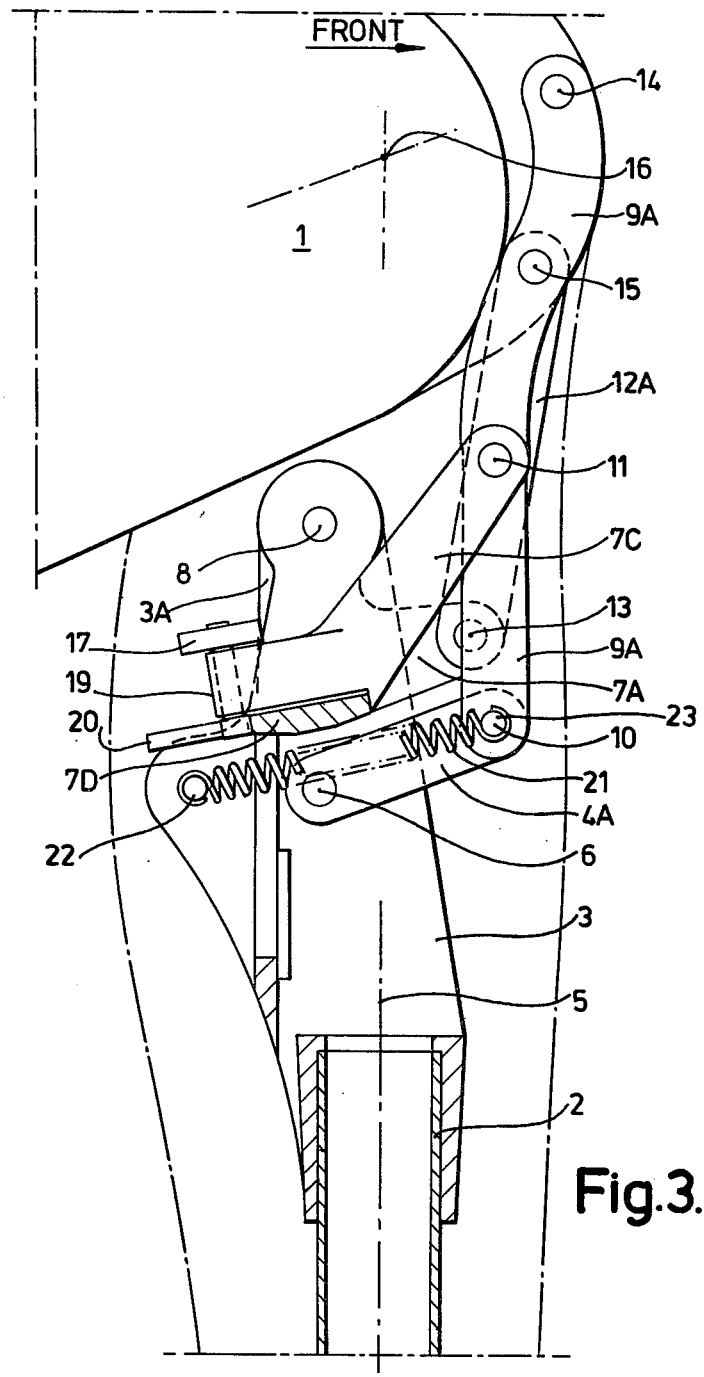
FIG. 3 is similar to FIG. 1, but in the position of full flexion.

It will be seen that the pivot connections at 14 and 15 are located adjacent the lower perimeter of the upper leg component 1, and that the members 9A and 9B are shaped to conform with that perimeter when the leg is in its fully flexed position (FIG. 3).

The construction of link III of the mechanism is best understood by comparing the three figures in relation to each other. The two side members 7A and 7B (only 7A appears in FIGS. 1 and 3) are pivotally mounted on the side arms 3A and 3B of the shin cradle, the pivoting axis being the axis 8. In the fully extended position of the leg (FIG. 1), the side members 7A and 7B extend in the anterior direction and at the rear surface of the calf are joined to the cross member 7D (shown in section). Below the junction with the cross-member 7D, each side member is pivotally connected to link V, this connection being defined by the axis 13. The third pivotal connection of link III is made via the central member 7C, which in FIG. 1 extends downwardly and forwardly from the cross member 7D to the said third pivotal connection defined by the axis 11. The central member 7C also carries at its upper end (FIG. 1) a simple manual knee lock device. (This device is not shown in FIG. 2). The device comprises a rectangular locking member 17 mounted on the end of a shaft 18 which is rotatable in a boss 19 in the top of the central member 7C. An operating lever 20 is fitted to the rear end of the shaft 18. From FIG. 1 it can be seen that in the fully extended position of the leg the locking member 17 is situated immediately in front of the front edges of the members 12A and 12B of link V. In the Figures the device is in its unlocked position. Rotation of the lever 20 through 90° causes the locking member 17 to move across the front edges of the members 12A and 12B thereby preventing the normal forward movement of the latter which occurs when the leg is flexed (see FIG. 3).

The mechanism in the drawing also incorporates a "kicker" spring 21 which biases the leg towards full extension. The spring 21 is attached at one end to a shaft 22 (not shown in FIG. 2) extending between the two arms 3A and 3B of the shin cradle 3 and at its other end to the shaft 23 which serves to connect link II to link IV.

We claim:

1. An artificial leg comprising:
    an upper leg component to be fitted to the patient's stump;
    a lower leg component including a shin member portion; and
    a knee mechanism connecting the upper leg component to the lower leg component to allow rotation of one component relative to the other;
    the knee mechanism being in the form of a multi-bar linkage defining a knee axis of rotation which is essentially stationary relative to the lower leg component over the complete range of knee flexion; and
    the said mechanism being located below said axis of rotation.

2. An artificial leg according to claim 1 wherein the knee axis of rotation lies outside the physical confines of the mechanism over the complete range of knee flexion.

3. An artificial leg according to claim 2 wherein the knee axis of rotation passes through the space provided for the patient's stump.

4. An artificial leg according to claim 1 wherein the linkage is a six-bar linkage.

5. An artificial leg according to claim 1 wherein:
    the linkage is a six-bar linkage;
    two links of the linkage are constituted by said upper leg component and said lower leg component;
    the other four links of the linkage are constituted by a plurality of pivotally interconnected members which are movable with respect to both the upper and lower leg components; and
    two of said other four links each have three pivot axes defining pivot connections with other links of the linkage.

6. An artificial leg according to claim 5 wherein the said other four links each comprise a pair of movable members laterally spaced with respect to each other on either side of the longitudinal axis of the shin.

7. An artificial leg according to claim 6 wherein one of the links having three pivot axes comprises, in addition to a pair of movable side members, a central movable member rigidly connected to each of the said pair of movable side members by a cross member.

8. An artificial leg according to claim 7 wherein the mechanism has a knee locking device mounted on the said central movable member and operable to engage another part of the mechanism when the leg is in its fully extended position, thereby preventing flexion of the knee until the device is released.

9. An artificial leg according to claim 5 wherein the mechanism includes extension bias means.

10. An artificial leg according to claim 9 wherein the extension bias means is a spring attached at one end to the lower leg component and at its other end to a shaft forming the pivot between two movable members of the linkage.

11. An artifial leg according to claim 5 wherein the mechanism includes a swing control device.

12. An artificial leg comprising:
   an upper leg component for attachment to a patient's thigh stump;
   a lower leg component forming a shin member portion;
   an arrangement of pivoting links connecting said upper and lower leg components;
   said links and leg components together constituting a six-bar linkage defining a knee axis of rotation about which said lower leg component is rotatable relative to said upper leg component; and
   the geometry of the linkage being such that said knee axis is projected to a position above and outside the physical confines of the linkage and remains essentially stationary relative to the lower leg component throughout the range of knee flexion of the leg.

13. A artificial leg according to claim 12 wherein said knee axis passes through a region which in use of the leg is occupied by the patient's thigh stump, said system of links being accommodated internally below said axis.

* * * * *